(12) United States Patent  
Fletcher et al.

(10) Patent No.: US 11,806,642 B2  
(45) Date of Patent: Nov. 7, 2023

(54) VENTING SYSTEM FOR A MIXING APPARATUS

(71) Applicant: FUJIFILM Irvine Scientific, Inc., Santa Ana, CA (US)

(72) Inventors: Thomas Reid Fletcher, Newport Beach, CA (US); Wayne Mauro, Santa Ana, CA (US); David Neese, Santa Ana, CA (US)

(73) Assignee: FUJIFILM IRVINE SCIENTIFIC, INC., Santa Ana, CA (US)

( * ) Notice: Subject to any disclaimer, the term of this patent is extended or adjusted under 35 U.S.C. 154(b) by 246 days.

(21) Appl. No.: 17/271,963

(22) PCT Filed: Aug. 30, 2019

(86) PCT No.: PCT/US2019/049122  
§ 371 (c)(1),  
(2) Date: Feb. 26, 2021

(87) PCT Pub. No.: WO2020/047448  
PCT Pub. Date: Mar. 5, 2020

(65) Prior Publication Data  
US 2021/0322897 A1  Oct. 21, 2021

Related U.S. Application Data

(60) Provisional application No. 62/725,717, filed on Aug. 31, 2018.

(51) Int. Cl.  
*B01D 53/22* (2006.01)  
*B01D 19/00* (2006.01)  
(Continued)

(52) U.S. Cl.  
CPC .......... *B01D 19/0031* (2013.01); *A61L 2/022* (2013.01); *B01D 61/20* (2013.01);  
(Continued)

(58) Field of Classification Search  
CPC .......... B01D 63/067; B01D 2311/2653; B01D 61/20; B01D 19/0031; B01D 2313/90;  
(Continued)

(56) References Cited

U.S. PATENT DOCUMENTS 4,276,170 A   6/1981  Vaillancourt  
5,603,900 A   2/1997  Clark et al.  
(Continued)

FOREIGN PATENT DOCUMENTS

CN    103127771      6/2013  
JP    2016-501125 A  1/2016  
WO    WO-2014/088882 A2  6/2014

OTHER PUBLICATIONS

Examination Report dated Aug. 24, 2022 issued in IN Application No. 202117007834, 7 pages.  
(Continued)

*Primary Examiner* — Anthony R Shumate  
(74) *Attorney, Agent, or Firm* — FOLEY & LARDNER LLP

(57) ABSTRACT

A filter unit for a mixing apparatus includes a hydrophilic filter and a hydrophobic vent filter. The hydrophilic filter is configured to receive a fluid including a liquid and gas. The hydrophilic filter is further configured to sterilize the liquid. The hydrophobic vent filter is configured to receive the gas from the hydrophilic filter. The hydrophobic vent filter further includes a vent and a membrane configured to separate an interior of the filter unit from an exterior of the filter unit, the gas being vented from the filter unit by flowing across the membrane and out of the vent. In some embodiments, the filter unit further includes a defoaming device configured to receive gas, foam comprised the liquid con-  
(Continued)

taining trapped gas, and some of the liquid from the hydrophilic filter and is further configured to release at least some of the gas from the foam.

17 Claims, 5 Drawing Sheets

(51) Int. Cl.
*A61L 2/02* (2006.01)
*B01D 61/20* (2006.01)
*B01D 63/06* (2006.01)
*B01D 71/34* (2006.01)
*B01D 71/36* (2006.01)
*B01D 71/68* (2006.01)

(52) U.S. Cl.
CPC ........... *B01D 63/067* (2013.01); *B01D 71/34* (2013.01); *B01D 71/36* (2013.01); *B01D 71/68* (2013.01); *B01D 2311/2653* (2013.01); *B01D 2313/16* (2013.01); *B01D 2313/90* (2013.01)

(58) Field of Classification Search
CPC .... B01D 2313/16; B01D 71/36; B01D 71/68; B01D 71/34; A61L 2/022
See application file for complete search history.

(56) References Cited

U.S. PATENT DOCUMENTS

| | | | | |
|---|---|---|---|---|
| 10,926,222 | B1* | 2/2021 | Bader | B01D 61/10 |
| 2001/0037966 | A1* | 11/2001 | Petersen | B01D 61/20 |
| | | | | 210/195.2 |
| 2002/0096467 | A1* | 7/2002 | Cappia | B01D 69/12 |
| | | | | 210/321.6 |
| 2004/0188344 | A1* | 9/2004 | Scott | B01D 63/08 |
| | | | | 210/406 |
| 2006/0043021 | A1* | 3/2006 | Pesakovich | B01D 65/00 |
| | | | | 210/321.75 |
| 2006/0063252 | A1* | 3/2006 | Ito | C12N 5/0075 |
| | | | | 435/325 |
| 2006/0090645 | A1 | 5/2006 | Kent | |
| 2008/0038821 | A1* | 2/2008 | Tachaboonyakiat | C08B 37/0012 |
| | | | | 435/378 |
| 2009/0324493 | A1* | 12/2009 | Burke | G21G 4/08 |
| | | | | 424/1.61 |
| 2010/0087473 | A1* | 4/2010 | Leverd | A61K 9/19 |
| | | | | 514/283 |
| 2012/0022449 | A1 | 1/2012 | Kim | |
| 2013/0134087 | A1 | 5/2013 | Porter et al. | |
| 2016/0243502 | A1 | 8/2016 | Vincent et al. | |
| 2016/0271638 | A1* | 9/2016 | Erlandson | B05B 15/30 |
| 2016/0311588 | A1* | 10/2016 | Wochele | A61J 1/1412 |
| 2017/0145368 | A1 | 5/2017 | Fletcher | |
| 2017/0319985 | A1 | 11/2017 | Perreault et al. | |
| 2019/0001290 | A1 | 1/2019 | Fletcher | |
| 2020/0198858 | A1* | 6/2020 | Lausted | B65D 51/1605 |
| 2021/0299614 | A1* | 9/2021 | Scott | B01D 63/087 |

OTHER PUBLICATIONS

International Search Report on PCT PCT/US2019/049122 dated Dec. 12, 2019, 4 pages.
Written Opinion of the International Searching Authority on PCT/US2019/049122 dated Dec. 12, 2019, 10 pages.
Foreign Action other than Search Report on CN 201980069410.2 dated Jun. 29, 2022.
Foreign Action other than Search Report on SG 11202101676T dated Jul. 17, 2022.
Foreign Action other than Search Report on non-Foley case related to EP 19769318.7 dated Jun. 14, 2022.
International Preliminary Report on Patentability received in corresponding International Application No. PCT/US2019/049122 dated Mar. 11, 2021, 12 pages.
Communication pursuant to Article 94(3) EPC dated Apr. 4, 2023 issued in EP Application No. 19769318.7, 7 pages.
Second Office Action dated Jan. 18, 2023 issued in CN Application No. 201980069410.2, with English translation, 7 pages.
Notice of Reasons for Refusal dated Jun. 20, 2023 issued in JP Application No. 2021-510353, with English translation, 10 pages.
Rejection Decision dated Apr. 15, 2023 issued in CN Application No. 201980069410.2, with English translation, 14 pages.
Examination Report No. 1 dated Aug. 8, 2023 issued in AU Application No. 2019331886, 3 pages.

* cited by examiner

VENTING SYSTEM FOR A MIXING APPARATUS

CROSS-REFERENCE TO RELATED APPLICATION

The present application is a U.S. National Stage of International Application No. PCT/US2019/049122 filed on Aug. 30, 2019, which claims the benefit of U.S. Provisional Patent Application No. 62/725,717 filed on Aug. 31, 2018, the entire disclosures of all of which are incorporated herein by reference.

BACKGROUND

Embodiments of the present technology generally relate to components for an automated method and apparatus for mixing at least one material with at least one fluid. More particularly, embodiments of the present technology relate to sterilization and/or filtration components for an automated method and apparatus specifically adapted for reconstituting dry ingredients into bioprocess solutions.

A bioprocess is a process that uses living cells or their components to obtain desired products. Bioprocesses often require the use of various solutions. For example, the initial steps in a bioprocess may involve cell culturing, and cell culturing often requires the use of cell culture media to successfully cultivate new cells. Later steps in a bioprocess may then require the use of various buffer solutions as part of a product purification process.

Bioprocess solutions are often hydrated from dry ingredients immediately before use either in large stainless steel tanks or in single-use mixing devices. The typical process is time-consuming, expensive, and adds no direct value to the desired product.

While the basic cell culture methods have not changed appreciably over the years, the volumes of cell cultures continue to increase dramatically, thereby changing the requirements for media preparation. Not only are more research laboratories, pharmaceutical, and biotechnology companies employing cell culture methods, but they are often doing so on a very large scale. A biotechnology company may consume many thousands of liters of liquid media a day and employ large numbers of manufacturing technicians and scientists to produce antibodies, growth factors, or recombinant proteins from cell culture for commercial use. The present disclosure provides an automated system and method for employing an in-line mixing device to prepare bioprocess solutions that can help reduce the required time, labor, risk of error and risk of contamination in these processes while also improving reliability and consistency.

Using an in-line mixing device requires venting gas, such as air, during a reconstitution process used, for example, to prepare a bioprocess solution. If not vented, air may displace the solution being reconstituted within the mixing device. Furthermore, air present in an in-line mixing device may not pass through filtration membranes (e.g., sterilizing hydrophilic membranes), causing the flow of the aqueous liquid in the mixing device to slow or even stop.

SUMMARY

Generally, embodiments described herein relate to components for automated methods and apparatuses for preparing dry ingredients into liquid solutions (e.g., preparing powdered bioprocess media into liquid bioprocess media). As discussed further below, dry ingredients tend to require less storage space than reconstituted, liquid solutions, have longer shelf lives, be less expensive, and require less shipping and handling time than prepackaged liquid solutions. Thus, when liquid solutions are needed, it is advantageous to utilize automated methods and apparatuses designed to make the preparation of liquid solutions from dry ingredients simple, straightforward, and repeatable, rather than purchase prepackaged liquid solutions. Accordingly, the technology according to some embodiments relates to components for an automated method for mixing dry ingredients (e.g., a powdered media) into a fluid, such as cell culture media or buffers. More particularly, some embodiments of the present technology relate to sterilization and/or filtration components for a mixing apparatus usable via an automated method, where both the automated method and the mixing apparatus are adapted for reconstituting dry ingredients into liquids in predetermined unit volume amounts.

A variety of dry ingredients may be reconstituted into liquid solutions using the present technology. For example, as used herein, dry ingredients may refer to powdered cell culture media, dry powder media, dry buffer powder, granulated media, dry salts, dry chemicals, dry components, dry materials, and unhydrated ingredients.

One embodiment relates to a filter unit for a mixing apparatus. The filter unit includes a hydrophilic filter and a hydrophobic vent filter. The hydrophilic filter is configured to receive a fluid including a liquid and gas. The hydrophilic filter is further configured to sterilize the liquid. The hydrophobic vent filter is configured to receive the gas from the hydrophilic filter. The hydrophobic vent filter further includes a vent and a membrane configured to separate an interior of the filter unit from an exterior of the filter unit, the gas being vented from the filter unit by flowing across the membrane and out of the vent.

Another embodiment relates to a filter unit for a mixing apparatus. The filter unit includes a hydrophilic filter, a defoaming device, and a hydrophobic vent filter. The hydrophilic filter is configured to receive a fluid including a liquid, gas, and foam comprised of the liquid containing trapped gas. The hydrophilic filter is further configured to sterilize the liquid. The defoaming device is configured to receive the gas, the foam, and some of the liquid from the hydrophilic filter. The defoaming device is further configured to release at least some of the gas from the foam. The hydrophobic vent filter is configured to receive the gas from the defoaming device. The hydrophobic vent filter further includes a vent and a membrane configured to separate an interior of the filter unit from an exterior of the filter unit, the gas being vented from the filter unit by flowing across the membrane and out of the vent.

Another embodiment relates to a method of filtering a solution. The method includes receiving, at a filter unit including of a hydrophilic filter, a defoaming device, and a hydrophobic vent filter, a fluid including a liquid, gas, and foam comprised of the liquid containing trapped gas; directing the gas and foam to the defoaming device, wherein the defoaming device is configured to release at least some of the gas from the foam; and venting the gas across a membrane and out of a vent of the hydrophobic vent filter, the membrane configured to separate an interior of the filter unit from an exterior of the filter unit. The method further includes sterilizing the liquid by the hydrophilic filter and evacuating the sterilized liquid from the filter unit.

BRIEF DESCRIPTION OF THE DRAWINGS

The above-mentioned features, as well as other features, aspects, and advantages, of the present technology will now

DETAILED DESCRIPTION

Figure 1:
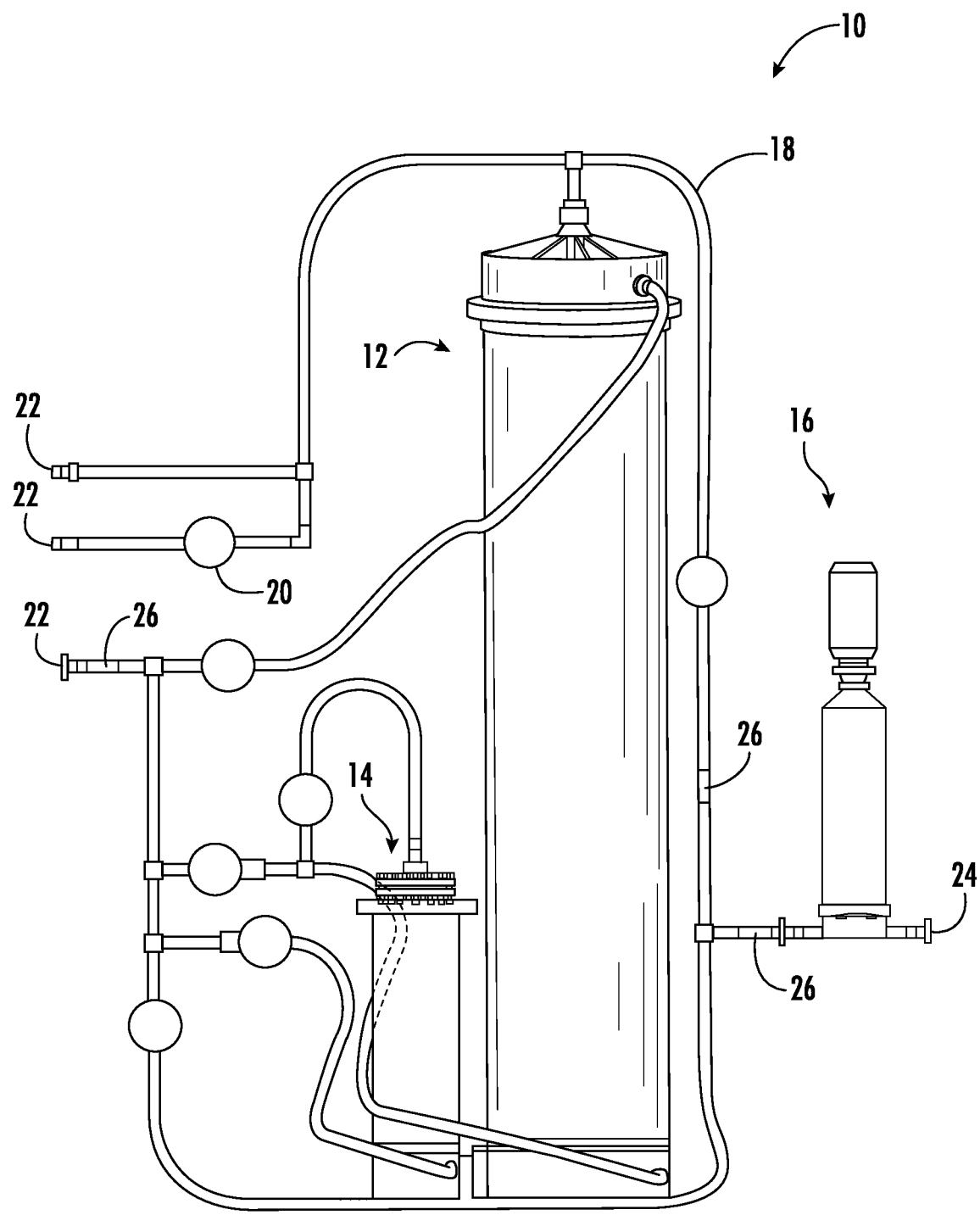
FIG. 1 is a schematic representation of a mixing apparatus including a filter unit for reconstituting a powder, such as a powdered bioprocess media, according to an exemplary embodiment.

In the following detailed description, reference is made to the accompanying drawings, which form a part of the present disclosure. In the drawings, similar symbols typically identify similar components, unless context dictates otherwise. The illustrative embodiments described in the detailed description, drawings, and claims are not meant to be limiting. The detailed description is intended as a description of exemplary embodiments and is not intended to represent the only embodiments that may be practiced. The term "exemplary," as used herein, means "serving as an example, instance, or illustration" and should not necessarily be construed as preferred or advantageous over other embodiments. Other embodiments may be utilized, and other changes may be made, without departing from the spirit or scope of the subject matter presented herein. It will be readily understood that the aspects of the present disclosure, as generally described herein and illustrated in the Figures, can be arranged, substituted, combined, and designed in a wide variety of different configurations, all of which are explicitly contemplated and form part of this disclosure.

Embodiments described herein generally relate to filtration and/or sterilization components for devices/apparatuses, systems, and methods used in the preparation of solutions from dry ingredients, for example, media for cell culture from dry powdered cell culture media or buffer solutions from dry buffer powder. One or more of the provided embodiments may overcome one or more of the drawbacks, limitations, or deficiencies that exist in the art with respect to reconstituting solutions, particularly with respect to reconstituting cell culture media in a dry format, including dry powder media. For example, in some embodiments described herein, components may facilitate the venting of gas, such as air, from an apparatus used to reconstitute a powder such that the reconstitution occurs more efficiently and produces a solution, for example, that does not contain unwanted foam or trapped gas, such as air.

The present disclosure makes reference to the systems and methods described herein in the context of preparing liquid cell culture media from powdered cell culture media. However, it should be understood that the systems and methods described herein can be adapted to preparing other types of solutions. For example, the systems and methods described herein may be used to prepare buffers for chromatography and downstream processing of biopharmaceutical bulk drug substances. As another example, the systems and methods described herein may be used to prepare various "bioprocess solutions," or solutions that are used in processes of using living cells or their components to obtain desired products. Moreover, it is contemplated that the systems and methods described herein may be adapted for a number of broader commercial or industrial applications. As an example, many liquid pharmaceuticals are prepared in the hospital pharmacy with some frequency and quantity. Saline solutions, alimentary preparations, imaging reagents, dyes, sterilization solutions, and anesthetics are reconstituted as liquids. Additional alternative applications include, but are not limited to, preparation of pesticides, fertilizers, and any of a variety of beverages commonly prepared from powder (e.g., milk, iced tea, etc.), all of which could be reconstituted using embodiments of the systems and methods described herein. In this regard, dry ingredients that may be reconstituted using the present systems and methods are not limited to powdered cell culture media and may include dry powder media, dry buffer powder, granulated media, dry salts, dry chemicals, dry components, dry materials, and unhydrated ingredients.

FIG. 1 is an overall system view of one embodiment of a mixing apparatus 10. Preferably, the mixing apparatus 10 is made of materials that are appropriate for the cell culture environment, such as non-toxic, medical grade plastics or other non-toxic materials that will not contaminate the media. The mixing apparatus 10 includes a first mixing chamber 12, a second mixing chamber 14, and a filter unit 16 connected together with various lengths of tubing 18 (e.g., flexible hoses). The tubing further includes various valves 20 provided therein for selectively allowing (e.g., when the valve is in an open position) and stopping (e.g., when the valve is in a closed position) the flow of fluids through the valves. In an exemplary embodiment, the valves are pinch valves, though in other embodiments, the valves may be or include other types of valves, such as ball valves. In various embodiments, the mixing apparatus 10 is designed for reconstitution of powdered cell culture media into liquid media. For example, the mixing apparatus 10 may be a single use apparatus with necessary media components (e.g., powdered cell culture media, sodium bicarbonate, etc.) prepackaged therein. However, those of skill in the art will appreciate that the mixing apparatus 10 may also be used to reconstitute other forms of undissolved cell culture media (e.g., granulated cell culture media), prepare bioprocessing buffers from a dry format, or more generally reconstitute liquids from powders.

To begin with, in various embodiments, the first mixing chamber 12 contains dry powder media to be reconstituted into liquid media. For example, the first mixing chamber 12 may be provided with a premeasured amount of dry powder media. In some embodiments, the first mixing chamber 12 may be prepackaged with the premeasured amount of dry powder media already therein. Additionally, in various embodiments, the first mixing chamber 12 is designed to facilitate mixing of the media with purified water and/or with other powders or liquids, such as dissolved sodium bicarbonate or a supplement. For example, the first mixing chamber 12 may include a top and/or bottom cone coupled to the top and/or bottom end, respectively, of the first mixing chamber 12 to facilitate the creation of a swirling vortex motion as fluid enters the first mixing chamber 12. The swirling vortex motion helps facilitate the mixing of the dry powder media, the purified water, dissolved sodium bicarbonate, a supplement, etc. Various configurations and embodiments of the first mixing chamber 12 are described in U.S. application Ser. No. 15/087,826 titled "Media Mixing Chamber," filed on Mar. 31, 2016, and hereby incorporated herein in its entirety.

The first mixing chamber 12 also includes various ports whereby fluids may flow into and out of the first mixing chamber 12, such as a top port, an upper port, and a lower port. In exemplary embodiments, at least some of the ports may be positioned on the first mixing chamber 12 such that fluids enter the first mixing chamber 12 at substantially a tangential angle to an inner wall of the first mixing chamber, which may further facilitate the mixing of various media components in the first mixing chamber. Additionally, the first mixing chamber 12 is connected via at least some of the ports with tubing 18 to various inlets 22, which may in turn be connected to various fluid sources for the reconstitution process, such as water, supplements for cell media, and compressed air to flush out remaining media from the apparatus 10 once the reconstitution process is completed.

In various embodiments, the second mixing chamber 14 contains an additive to the cell culture media. In an exemplary embodiment, the second mixing chamber 14 contains sodium bicarbonate powder, and the second mixing chamber 14 is designed to facilitate mixing of the sodium bicarbonate with purified water. Additionally, the second mixing chamber 14 may be prepackaged with a premeasured amount of sodium bicarbonate therein. In some embodiments, the second mixing chamber 14 is configured similarly to the first mixing chamber 12 (e.g., including a top and/or bottom cone coupled to the top and/or bottom end, respectively, of the second mixing chamber 14 to facilitate the creation of a swirling vortex motion as fluid enters the second mixing chamber 14). In other embodiments, the second mixing chamber 14 is configured differently from the first mixing chamber 12. Various configurations and embodiments of the second mixing chamber 14 are also described in U.S. application Ser. No. 15/087,826 titled "Media Mixing Chamber," filed on Mar. 31, 2016, which as noted above is incorporated herein in its entirety.

Similar to the first mixing chamber 12, the second mixing chamber 14 includes various ports whereby fluids may flow into and out of the second mixing chamber, such as a top port and a lower port. Additionally, at least some of the ports may also be positioned on the second mixing chamber 14 such that fluids enter the second mixing chamber 14 at substantially a tangential angle to an inner wall of the mixing chamber. The second mixing chamber 14 is further connected via at least some of the ports with tubing 18 to various of the inlets 22, such as an inlet connected to a water source. Moreover, as shown in FIG. 1, the first mixing chamber 12 and the second mixing chamber 14 may be connected to each other via their respective ports with tubing 18.

The apparatus 10 also includes the filter unit 16 positioned before an outlet 24 for the apparatus 10. The filter unit 16 is configured to filter reconstituted solution flowing into the filter unit 16. For example, in the embodiment shown in FIG. 1, fluid may flow into the filter unit 16 from the first mixing chamber 12 and/or a water source. The filter unit 16 may be further configured to sterilize the solution flowing into the filter unit 16. Additionally, as described in further detail below, the filter is configured to remove air or other gas from the solution. Once the reconstituted solution has been filtered and/or sterilized by the filter unit 16, the solution flows out of the apparatus 10 via the outlet 24 and, for example, is directed into a sterile storage container.

Additionally, in various embodiments, the mixing apparatus 10 may include various sensors for taking measurements in the mixing apparatus 10. These sensors may include, for example, pressure sensors (e.g., for detecting water pressure within the apparatus 10), conductivity sensors (e.g., for detecting the conductivity, and thus the concentration, of solutions in the apparatus 10), cumulative volume sensors, such as a rotary flow meter, (e.g., for detecting a volume and flow rate of fluid consumed in the mixing process), pH sensors (e.g., for detecting the pH of solutions in the apparatus 10), viscometers (e.g., for measuring the viscosity of fluids in the apparatus 10), and so on. For example, in the embodiment of FIG. 1, the apparatus 10 includes sensors 26 positioned as shown in the tubing 18. These sensors 26 may include a pressor sensor configured to measure the pressure of fluids flowing into the filter unit 16 (e.g., to ensure that the filter unit 16 backpressure does not become too high); a conductivity sensor configured to measure the conductivity of the solution flowing into the filter unit 16, thereby indirectly measuring the concentration of the solution flowing into the filter unit 16 and ultimately out of the apparatus 10; and a volume sensor configured to measure the volume and flow rate of water consumed during the mixing process.

In various embodiments, the powdered media are also mixed into liquid media in the mixing apparatus 10 through an automated method. For example, a computing system may control the opening and closing of valves, as well as fluid sources used during the automated method (e.g., a water source, a compressed air source, a supplement source), to control the mixing of the powdered media. The computing system may open and/or close valves and component sources in response to a variety of triggers. For example, the computing system may receive measurements from the mixing apparatus 10 related to the mixing process (e.g., from a pressure sensor, a conductivity sensor, and a volume sensor). The computing system may then open and/or close valves and/or fluid sources in response to receiving measurements of certain levels, below or above certain levels, within certain ranges, etc. As another example, the computing system may open and/or close valves and/or fluid sources in response to certain amounts of elapsed time.

Using the mixing apparatus 10 to prepare liquid media from dry powdered media through an automated method is an improvement over the current field, as it allows for easy and efficient liquid media preparation. Additionally, having programming logic (e.g., implemented by a processing circuit executing instructions stored on non-transitory machine readable media as part of a computing system) controlling the automated method makes the preparation of liquid media from dry powdered media repeatable and consistent. Additional detail on various configurations and embodiments of the mixing apparatus 10 and the automated method used with the mixing apparatus 10 are described in U.S. patent application Ser. No. 16/017,014, titled "Automated Method and Apparatus for Preparing Bioprocess Solutions," filed on Jun. 25, 2018, and hereby incorporated herein in its entirety.

Hydrating and filtering a powder, such as powdered cell culture media, in a closed or substantially closed system (e.g., mixing apparatus 10) requires venting gas, such as air. Air will not pass through a typical sterilizing hydrophilic membrane of a filter (e.g., filter unit 16) at normal operating pressures for sterile filtration of aqueous liquids. If the air is not removed by venting, the filter flow will be reduced and eventually stop as air displaces aqueous liquid on the upstream side of the filter. Additionally, the dry areas of the hydrophilic membrane will not allow aqueous liquid to pass through.

As such, to allow for efficient flow of liquid through a mixing apparatus, the filter for the apparatus needs an air vent. However, the vent must be selectively permeable for outbound air and not for inbound microorganisms, which could contaminate the solution in the apparatus and compromise the closed system. Additionally, the air vent should prevent discharge of aqueous liquid being mixed in the mixing apparatus.

In such situations, it has been determined that employing a semipermeable hydrophobic membrane with sufficiently small pores (e.g., 0.2 µm or less) can selectively allow air or other gas to vent and prevent both in-bound microbial contamination and discharge of aqueous liquid as long as the membrane is substantially dry and free of foam. However, the hydration of a powder, such as powdered cell culture media, produces a mixture of liquid and air that can generate very small gas bubbles and foam (e.g., solution liquid containing trapped air) that inhibit the venting of air through a hydrophobic membrane. The foam and bubbles wet the membrane, and wetted areas of the hydrophobic membrane will not allow air to pass through. Reduction of the vent flow rate causes accumulation of air in the system that, as noted above, displaces the aqueous liquid on the upstream side of the hydrophilic filter and ultimately reduces flow rates of the aqueous liquid filtrate. As such, it has further been determined that sufficient air venting can be sustained by employing a defoaming device immediately upstream of the hydrophobic vent filter. By helping to break small air bubbles and foam, the device effectively allows separation of aqueous liquid from air and can prevent wetting of the hydrophobic vent filter.

Figure 2:
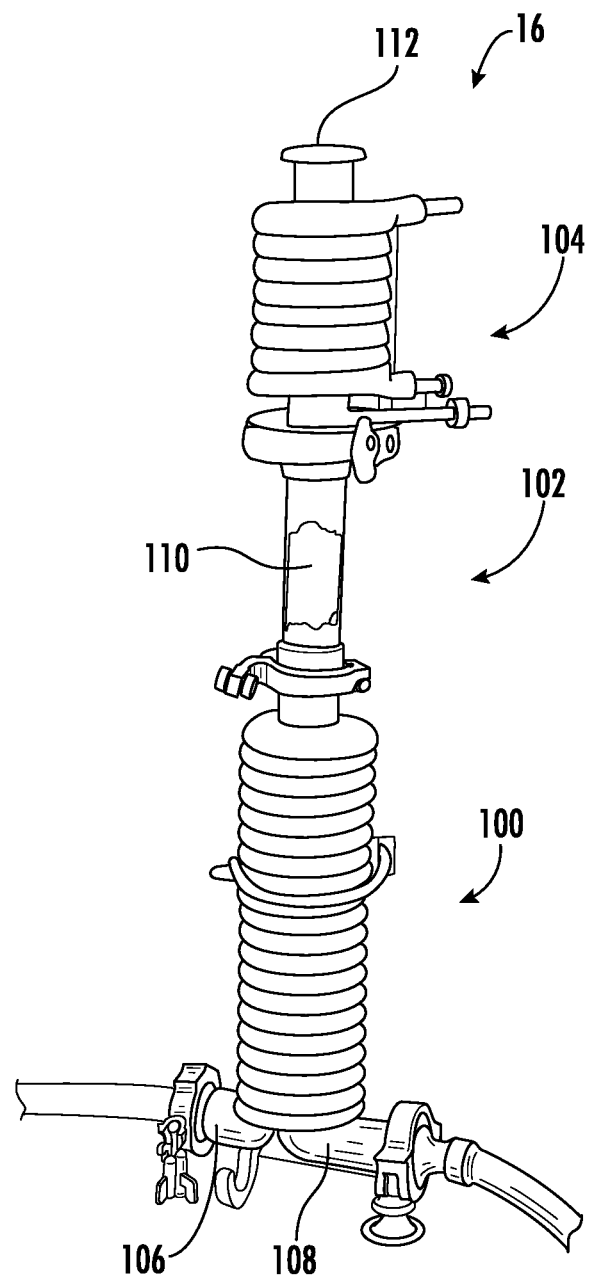
FIG. 2 is a detailed schematic representation of the filter unit of FIG. 1, according to an exemplary embodiment.
Figure 3:
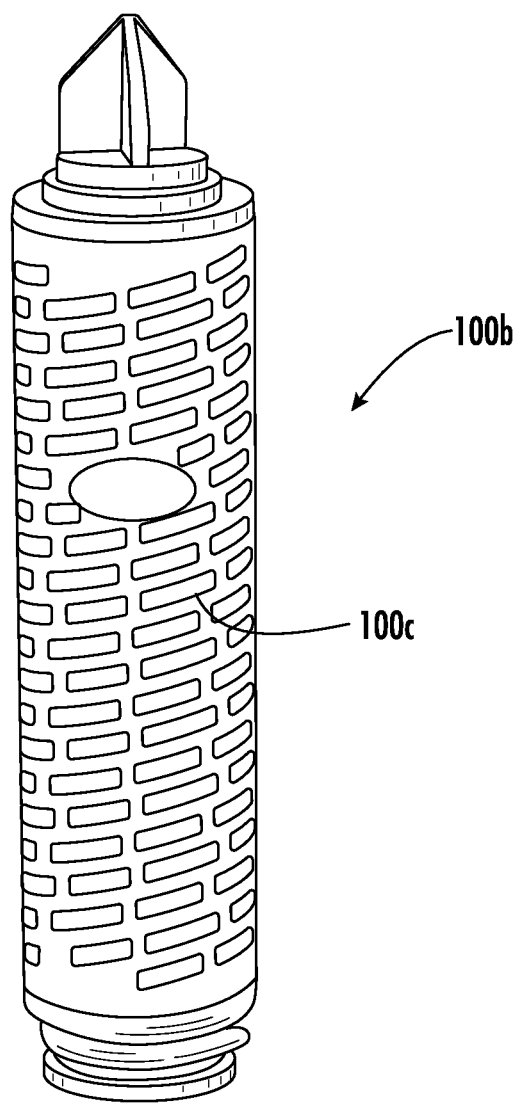
FIG. 3 is a perspective view of a filter element of the filter unit, according to an exemplary embodiment.
Figure 4:
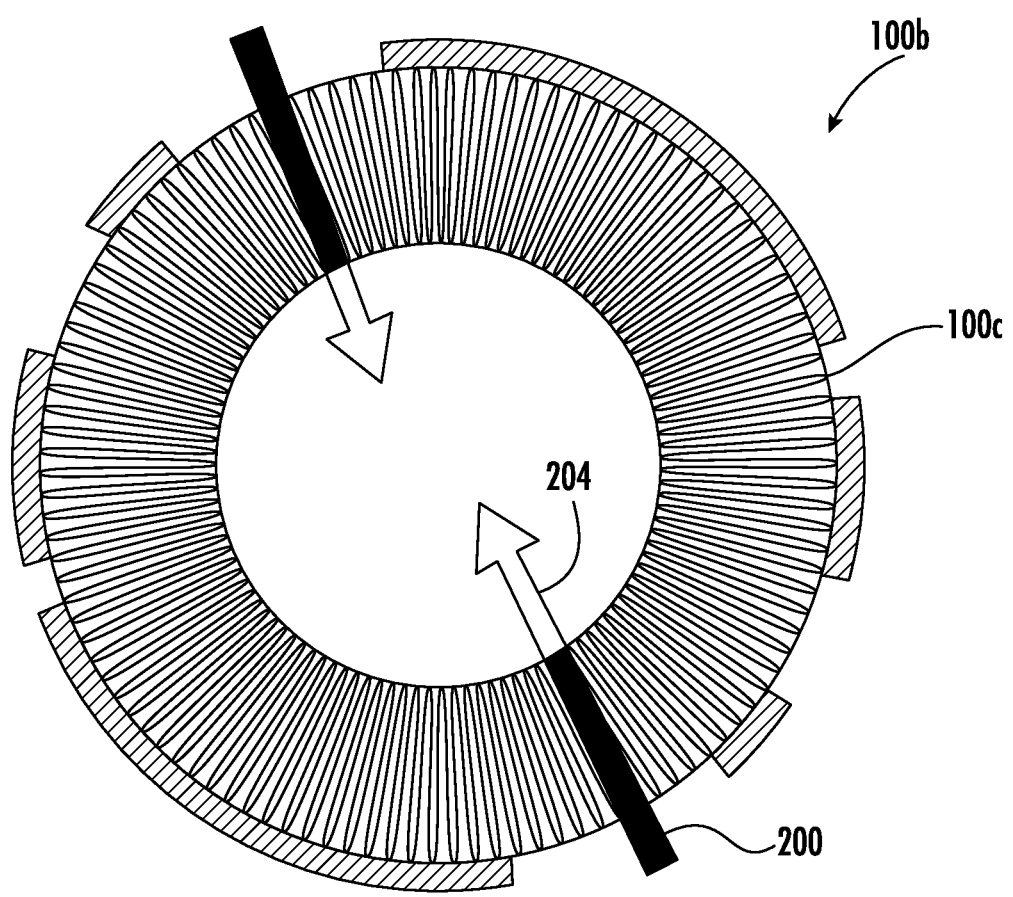
FIG. 4 is a cross-sectional view of the filter element of FIG. 3, according to an exemplary embodiment.
Figure 5:
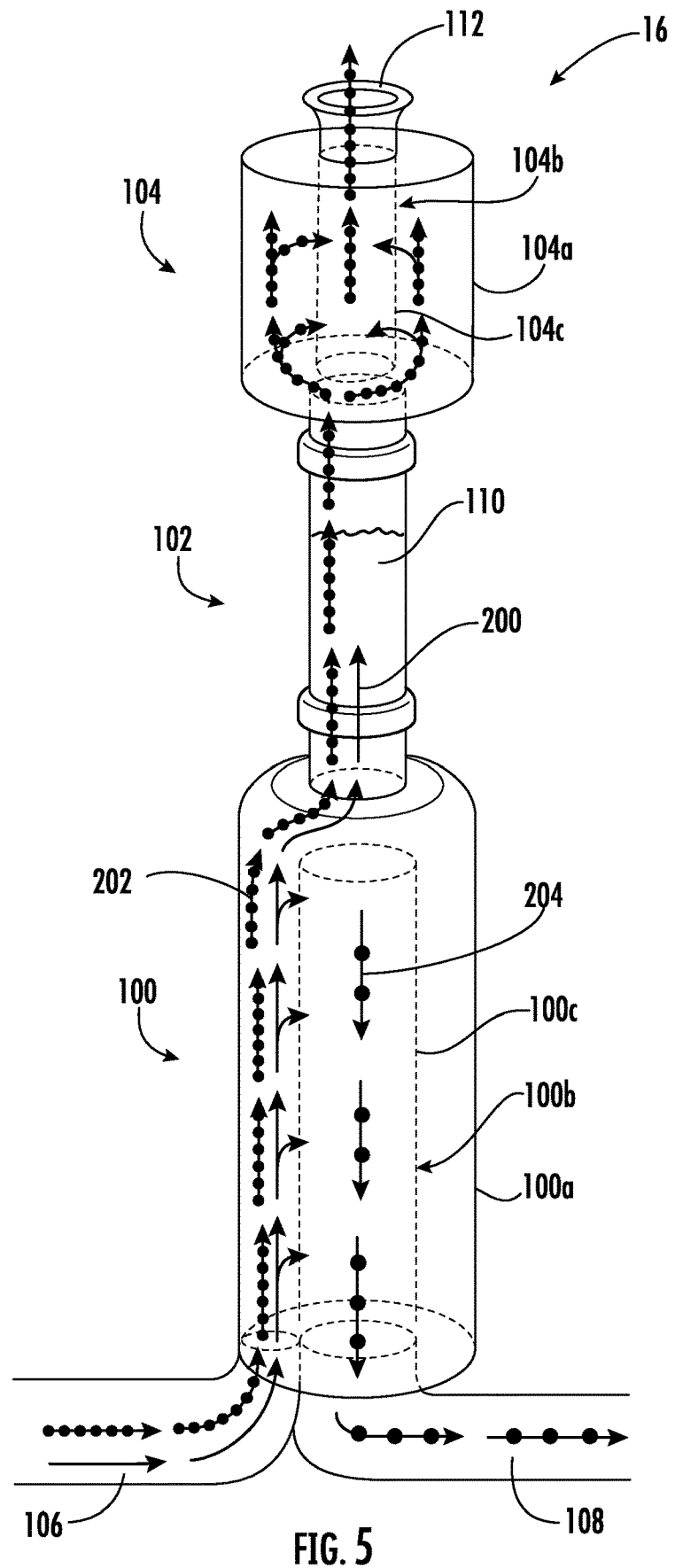
FIG. 5 is a detailed schematic representation of the filter unit of FIG. 1 depicting the flow of fluids within the filter, according to an exemplary embodiment.

FIG. 2 is a detailed view of the filter unit 16 incorporating these advantageous features. In various embodiments, the filter unit 16 includes a hydrophilic filter 100, a defoaming device 102, and a hydrophobic vent filter 104. The hydrophilic filter 100 is a sterilizing filter and includes a membrane for sterilizing incoming solution. In some embodiments, the hydrophilic filter 100 includes a hollow, cylindrical filter element 100b (not seen in FIG. 2). FIG. 3 and the cross-sectional view of FIG. 4 depict cylindrical filter element 100b, including a pleated membrane 100c (e.g., at the outer surface of the filter element). As shown in FIG. 5, hydrophilic filter 100 includes cylindrical filter element 100b that fits into a cylindrical filter capsule 100a such that there is space between the filter element 100b and the filter capsule 100a. The cylindrical filter element 100b includes membrane 100c that sterilizes solution coming into the hydrophilic filter 100. For example, the aqueous liquid entering the hydrophilic filter 100 passes through this membrane 100c of the cylindrical filter element 100b at 5-15 L/min. Accordingly, in various implementations, the solution enters the hydrophilic filter 100 via an inlet 106 into the space between the filter capsule 100a and the filter element 100b, is sterilized by passing through the membrane 100c of the filter element 100b into the hollow center of the filter element 100b, and is evacuated from the hydrophilic filter 100 via an outlet 108. In various embodiments, the hydrophilic filter element 100b is at least partially composed of a hydrophilic material such as polyethersulfone ("PES").

Referring again to FIG. 2, the defoaming device 102 contains a defoaming substance 110 configured to break up small air bubbles and foam in the solution to release air trapped therein. For example, in some embodiments, the defoaming substance may be steel wool or stainless steel shavings. Accordingly, the defoaming device 102 is configured to receive at least some of the solution from the hydrophilic filter 100, including any foam and air mixed in with the solution, and break up bubbles and foam in the solution to release air from the solution. As an illustration, the defoaming substance 110 may be configured to break up the air bubbles and foam through a combination of kinetic forces of the flowing solution and the structure of the defoaming substance 110.

The hydrophobic vent filter 104 is configured to vent air or other gas from the solution being mixed in the apparatus 10. For example, in some embodiments, the hydrophobic vent filter 104 may vent up to 50 L of air during a mixing process. As shown in FIG. 5, in some embodiments, the hydrophobic vent filter 104 includes a cylindrical filter element 104b (including a membrane at an outer surface of the filter element 104b, similar to filter element 100b and membrane 100c) that fits into a cylindrical filter capsule 104a. Thus, in various implementations, air (and any solution incidentally pushed or sprayed into the hydrophobic vent filter 104) from the hydrophilic filter 100 enters the hydrophobic vent filter 104 into the space between the filter capsule 104a and the filter element 104b. The air then flows through the membrane of filter element 104b into the hollow center inside the filter element 104b and then out of the hydrophobic vent filter 104, and thus the apparatus 10, through a vent 112 positioned on the top of the hydrophobic vent filter 104 (e.g., incorporated as part of the filter capsule 104a). Additionally, the membrane 104c separates an interior of the filter unit 16 from an exterior of the filter unit 16 such that, for example, microbes and unwanted particulates do not enter the apparatus 10 and compromise the closed system of the apparatus 10. In various embodiments, the hydrophobic vent filter element 104b is at least partially composed of a hydrophobic material such as polytetrafluoroethylene ("PTFE") or polyvinylidene fluoride ("PVDF").

FIG. 5 illustrates the flow of solution and air through the filter unit 16. In the embodiment of FIG. 5, the flow of unsterilized solution is illustrated by solid arrows 200, the flow of air or other gas is illustrated by dotted arrows 202, and the flow of sterilized solution is illustrated by dotted arrows 204. Additionally, FIG. 5 illustrates both the filter capsule 100a, 104a and the filter element 100b, 104b for each of the hydrophilic filter 100 and the hydrophobic vent filter 104. As shown, the hydrophilic filter 100 includes hydrophilic filter capsule 100a and hydrophilic filter element 100b, and the hydrophobic vent filter 104 includes hydrophobic filter capsule 104a and a hydrophobic filter element 104b.

As shown in FIG. 5, unsterilized solution 200 and air or other gas 202 enters into the hydrophilic filter 100 through the inlet 106. The unsterilized solution 200 fills the space between the hydrophilic filter capsule 100a and the hydrophilic filter element 100b. The unsterilized solution 200 passes through the membrane 100c of the hydrophilic filter element 100b (e.g., at a rate of 5-15 L/min), thereby becoming sterilized, and into the hollow center within the hydrophilic filter element 100b. The sterilized solution 204 is then evacuated out of the filter unit 16 by flowing through the outlet 108 (e.g., coupled to an outlet port on the hydrophilic filter capsule 100a through which the sterilized solution is evacuated from the hydrophilic filter 100). The sterilized filtrate 204 may then be collected in a sterile vessel and, for example, used as part of a bioprocess.

Additionally, the unsterilized solution 200 and any air or other gas 202 can flow from the hydrophilic filter 100 into the defoaming device 102. In practice, for example, the air and any bubbles or foam may rise from the unsterilized solution 200 in the hydrophilic filter 100 into the defoaming device 102. The defoaming substance 110 in the defoaming device 102 breaks up bubbles and foam in the solution, thereby releasing the air 202 trapped within and allowing the unsterilized solution to flow back into the hydrophilic filter 100.

The air or other gas 202 then flows into the hydrophobic vent filter 104 (e.g., along with small amounts of unsterilized solution also pushed or sprayed into the hydrophobic vent filter 104). As shown in FIG. 5, the air 202 flows into the space between the hydrophobic filter capsule 104a and the hydrophobic filter element 104b. The air flows through the membrane 104c of the hydrophobic filter element 104b into the hollow center of the hydrophobic filter element 104b. The membrane (e.g., a 0.2 µm barrier) of the hydrophobic filter element 104b prevents bacteria and other microbes from entering the apparatus 10. The air then flows out of the center of the hydrophobic filter element 104b and through the vent 112, thereby leaving the apparatus 10.

In this way, the filter unit 16 is able to separate and vent air from mixed solution, as well as sterilize the solution, while preserving the closed system of the mixing apparatus 10. The filter unit 16 composed of the hydrophilic filter 100, defoaming device 102, and hydrophobic vent filter 104 thus provides the technical advantages discussed above. In addition, in some embodiments, the above-described configuration of the filter unit 16 represents an unusual approach for sterilization of solution and venting of air during a mixing process because many hydrophobic filters may be recommended for performance in dry conditions only. For example, while hydrophobic filters may be tested to measure the minimum "breakthrough pressure" of water, it may be recommended that many hydrophobic filters do not get wet because moisture can potentially affect the performance of the hydrophobic filters. By contrast, in the filter unit 16 described above, while the hydrophobic vent filter 104 is not directly configured to receive the flow of unsterilized solution, the hydrophobic vent filter 104 may still contact some of the unsterilized solution from the defoaming device 102 (e.g., because the unsterilized solution is sprayed into the hydrophobic vent filter 104 due to kinetic forces of the flow of the unsterilized solution). As such, the above-described configuration of the filter unit 16 may be unusual in filtration systems. However, this configuration may allow the apparatus 10 to effectively vent air, as well as separate trapped air from mixed solution, while maintaining the solution inside the apparatus 10 and maintaining a closed system as described above. Accordingly, this configuration may be advantageous for many applications of the apparatus 10.

Alternatively, in some embodiments, the filter unit 16 may not include the defoaming device 102. Instead, the hydrophilic filter 100 may be directly connected to the hydrophobic vent filter 104 (not shown). In such embodiments, the unsterilized solution may be more likely to spray or flow into the hydrophobic vent filter 104, thus increasing the unexpectedness of using such a configuration. However, this configuration may allow solution to be effectively sterilized and air vented, for example, in situations where foaming is of less concern or less of an issue.

It should also be understood that, in some embodiments, the filter unit 16 may be arranged in other configurations different from the filter unit 16 shown in FIGS. 2 and 3. For example, in some embodiments, no sterilization of the solution being mixed in the apparatus 10 may be necessary. As such, the filter unit 16 may include the defoaming device 102 and the hydrophobic vent filter 104 but not the hydrophilic filter 100. Alternatively, in other embodiments, the filter unit 16 may include different or additional components, such as multiple vents. Additionally, it should be understood that in other embodiments, the apparatus 10 may be configured differently than the apparatus 10 shown in FIG. 1. For example, in some embodiments, the filter unit 16 may be located in a different section of the apparatus 10.

Furthermore, while the above embodiments are described with reference to the reconstitution of powdered cell culture media, it should be understood that embodiments of the mixing apparatus 10 and the filter unit 16 may be used with automated method embodiments to reconstitute a variety of dry ingredients into liquids, such as a variety of bioprocess powders into bioprocess solutions. It is further contemplated that the liquid solvents employed can be water, alcohols, or other organics. The solubility characteristics, the solvent to be used, the amount required, and the chemical interactions between the solvent and the reconstituted chemicals will serve to provide guidelines for the configuration of the mixing apparatus 10 and/or the filter unit 16, as well as any automated methods used to reconstitute the powders using the apparatus 10.

The filter unit 16 may comprise nylon or cellulose acetate. Additionally, for a media product, the membrane(s) used in the filter unit 16 may be 0.2 µm filters, though it is contemplated that other filter sizes could be chosen for certain functions. For example, the preparation of electrophoretic buffers requires clean, but not necessarily sterile solutions, and a 0.45µ filter would be adequate. Similarly, the preparation of more viscous solutions may necessitate a wider pore size. In short, the membrane(s) used in the filter unit 16 can be of any desired size, volume, pore size, and so forth.

It will be appreciated by those skilled in the art that various modifications and changes may be made without departing from the scope of the described technology. Such modifications and changes are intended to fall within the scope of the embodiments, as defined by the appended claims. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged, or excluded from other embodiments.

The embodiments herein have been described with reference to drawings. The drawings illustrate certain details of specific embodiments that implement the systems and methods described herein. However, describing the embodiments with drawing should not be construed as imposing on the disclosure any limitations that may be present in the drawings.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims, are generally intended as "open" terms (e.g., the term "including" should be interpreted as "including but not limited to," the terms "comprising" and "having" should, respectively, be interpreted as "comprising at least" and "having at least," the term "includes" should be interpreted as "includes but it not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be constructed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an." In general, "a" and/or "an" should be interpreted to mean "at least one" or "one or more"; the same holds true for the use of definite articles used to introduce claim recitations.

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibility of including one of the terms, either of the terms, or both terms. For example, the phrase "A or B" will be understood to include the possibilities of "A" or "B" or "A and B."

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another, or with the two members or the two members and any additional intermediate members being attached to one another. Such joining may be permanent in nature or may be removable or releasable in nature.

The technology discussed herein has numerous applications and while particular embodiments of the technology have been described in detail, it will be apparent to those skilled in the art that the disclosed embodiments may be modified given the design considerations discussed herein. Therefore, the foregoing description is to be considered exemplary rather than limiting, and the true scope of the invention is that defined in the following claims.

What is claimed is:

1. A filter unit for a mixing apparatus comprising:
   a hydrophilic filter configured to receive a fluid including a liquid and gas, the hydrophilic filter further configured to sterilize the liquid,
      wherein the hydrophilic filter comprises a hollow cylindrical filter element disposed within a cylindrical filter capsule, the filter capsule comprising an outlet port and the filter element comprising a second membrane configured to sterilize the liquid; and
      wherein the filter element is coupled to the filter capsule such that the liquid is evacuated from the filter unit by flowing across the second membrane into a hollow center of the filter element and out of the outlet port; and
   a hydrophobic vent filter configured to receive the gas from the hydrophilic filter, the hydrophobic vent filter further comprising a vent and a membrane configured to separate an interior of the filter unit from an exterior of the filter unit, the gas being vented from the filter unit by flowing across the membrane and out of the vent.

2. The filter unit of claim 1, wherein the hydrophobic vent filter is configured to receive some of the liquid from the hydrophilic filter.

3. The filter unit of claim 1, wherein the hydrophobic vent filter is at least partially composed of at least one of polytetrafluoroethylene or polyvinylidene fluoride.

4. The filter unit of claim 1, wherein the hydrophilic filter is at least partially composed of a polyethersulfone.

5. The filter unit of claim 1, wherein the hydrophobic vent filter further comprises a hollow cylindrical filter element disposed within a cylindrical filter capsule, the filter capsule comprising the vent and the filter element comprising the membrane; and
   wherein the filter element is coupled to the filter capsule such that gas is vented from the filter unit by flowing across the membrane into a hollow center of the filter element and out of the vent.

6. A filter unit for a mixing apparatus comprising:
   a hydrophilic filter configured to receive a fluid including a liquid, gas, and foam comprised of the liquid containing trapped gas, the hydrophilic filter further configured to sterilize the liquid,
      wherein the hydrophilic filter comprises a hollow cylindrical filter element disposed within a cylindrical filter capsule, the filter capsule comprising an outlet port and the filter element comprising a second membrane configured to sterilize the liquid; and
      wherein the filter element is coupled to the filter capsule such that the liquid is evacuated from the filter unit by flowing across the second membrane into a hollow center of the filter element and out of the outlet port;
   a defoaming device configured to receive the gas, the foam, and some of the liquid from the hydrophilic filter, the defoaming device further configured to release at least some of the gas from the foam; and
   a hydrophobic vent filter configured to receive the gas from the defoaming device, the hydrophobic vent filter further comprising a vent and a membrane configured to separate an interior of the filter unit from an exterior of the filter unit, the gas being vented from the filter unit by flowing across the membrane and out of the vent.

7. The filter unit of claim 6, wherein the hydrophobic vent filter is configured to receive some of the liquid from the defoaming device.

8. The filter unit of claim 6, wherein the defoaming device contains a defoaming substance configured to release the at least some of the gas from the foam.

9. The filter unit of claim 8, wherein the defoaming substance comprises stainless steel shavings.

10. The filter unit of claim 6, wherein the hydrophobic vent filter is at least partially composed of at least one of polytetrafluoroethylene or polyvinylidene fluoride.

11. The filter unit of claim 6, wherein the hydrophilic filter is at least partially composed of a polyethersulfone.

12. The filter unit of claim 6, wherein the hydrophobic vent filter further comprises a hollow cylindrical filter element disposed within a cylindrical filter capsule, the filter capsule comprising the vent and the filter element comprising the membrane; and wherein the filter element is coupled to the filter capsule such that gas is vented from the filter unit by flowing across the membrane into a hollow center of the filter element and out of the vent.

13. A method of filtering a solution comprising:

receiving, at a filter unit comprised of a hydrophilic filter, a defoaming device, and a hydrophobic vent filter, a fluid including a liquid, gas, and foam comprised of the liquid containing trapped gas, wherein the hydrophilic filter comprises a hollow cylindrical filter element disposed within a cylindrical filter capsule, the filter capsule comprising an outlet port and the filter element comprising a second membrane configured to sterilize the liquid;

directing the gas and foam to the defoaming device, wherein the defoaming device is configured to release at least some of the gas from the foam;

venting the gas across a membrane and out of a vent of the hydrophobic vent filter, the membrane configured to separate an interior of the filter unit from an exterior of the filter unit;

sterilizing the liquid by the hydrophilic filter, wherein sterilizing the liquid comprises flowing the liquid across the membrane into a hollow center of the filter element; and evacuating the sterilized liquid from the filter unit, wherein evacuating the sterilized liquid comprises evacuating the liquid out of the outlet port.

14. The method of claim 13, wherein the hydrophobic vent filter is configured to receive some of the liquid.

15. The method of claim 13, wherein the defoaming device contains a defoaming substance configured to release the at least some of the gas from the foam.

16. The method of claim 13, wherein the hydrophobic vent filter is at least partially composed of at least one of polytetrafluorethylene or polyvinylidene fluoride.

17. The method of claim 13, wherein the hydrophobic vent filter further comprises a hollow cylindrical filter element disposed within a cylindrical filter capsule, the filter capsule comprising the vent and the filter element comprising the membrane; and wherein venting the gas comprises venting the gas across the membrane into a hollow center of the filter element and out of the vent.

* * * * *